United States Patent
Monteiro et al.

(10) Patent No.: US 9,919,066 B2
(45) Date of Patent: Mar. 20, 2018

(54) ELECTROPORATION OF TISSUE PRODUCTS

(71) Applicant: LifeCell Corporation, Branchburg, NJ (US)

(72) Inventors: Gary Monteiro, Branchburg, NJ (US); Martin J. Byrne, Hellertown, PA (US); Rick T. Owens, Stewartsville, NJ (US)

(73) Assignee: LifeCell Corporation, Branchburg, NJ (US)

( * ) Notice: Subject to any disclaimer, the term of this patent is extended or adjusted under 35 U.S.C. 154(b) by 252 days.

(21) Appl. No.: 14/762,235

(22) PCT Filed: Jan. 8, 2014

(86) PCT No.: PCT/US2014/010586
§ 371 (c)(1),
(2) Date: Jul. 21, 2015

(87) PCT Pub. No.: WO2014/116417
PCT Pub. Date: Jul. 31, 2014

(65) Prior Publication Data
US 2015/0343101 A1    Dec. 3, 2015

Related U.S. Application Data

(60) Provisional application No. 61/755,598, filed on Jan. 23, 2013.

(51) Int. Cl.
*A61L 2/00* (2006.01)
*A01N 25/00* (2006.01)
*A01N 37/16* (2006.01)

(52) U.S. Cl.
CPC ............ *A61L 2/0011* (2013.01); *A01N 25/00* (2013.01); *A01N 37/16* (2013.01); *A61L 2/007* (2013.01); *A61L 2/0088* (2013.01)

(58) Field of Classification Search
CPC ...... A61L 2/0011; A61L 2/0088; A61L 2/007; A01N 25/00; A01N 37/16
See application file for complete search history.

(56) References Cited

U.S. PATENT DOCUMENTS

2008/0166266 A1    7/2008    Burns et al.
2009/0234269 A1*   9/2009    Tavger .................. A61M 11/02
                                                   604/20

FOREIGN PATENT DOCUMENTS

GB          2469205 A        10/2010
WO     WO-2006/101885 A2     9/2006
(Continued)

OTHER PUBLICATIONS

Golberg et al.; "Irreversible Electroporation for Microbial Control of Drugs in Solution"; AAPS Pharm. Sci. Tech.; 10(3):881-886 (Sep. 2009).

(Continued)

*Primary Examiner* — Sean E Conley
(74) *Attorney, Agent, or Firm* — McCarter & English, LLP; Matthew R. Van Eman

(57) ABSTRACT

The present disclosure provides methods for reducing bioburden on a tissue product, as well as the tissue products produced according to the disclosed methods. In particular, the disclosure relates to methods of electroporating tissue in the presence of one or more bactericides in order to reduce bioburden. The methods allow for reduced exposure to electrical energy and/or bactericide while reducing bioburden.

25 Claims, 1 Drawing Sheet

(56) References Cited

FOREIGN PATENT DOCUMENTS

WO WO-2010/124346 A1 11/2010
WO WO-2011/022369 A2 2/2011

OTHER PUBLICATIONS

International Search Report and Written Opinion for International Patent Application No. PCT/US2014/010586, dated Apr. 4, 2014.
Kalchayanand et al.; "Hydrostatic Pressure and Electroporation Have Increased Bactericidal Efficiency in Combination with Bacteriocins"; Applied and Environmental Microbiology; 60(11):4174-4177 (1994).
Prausnitz et al.; "Electroporation of Mammalian Skin: A Mechanism to Enhance Transdermal Drug Delivery"; Proceedings of the National Academy of Sciences, National Academy of Sciences; 90(22)10504-10508 (1993).
Rowan et al.; "Pulsed Electric Field Inactivation of Diarrhoeagenic Bacillus Cereus Through Irreversible Electroporation"; Letters in Applied Microbiology; 31:110-114 (2000).

* cited by examiner

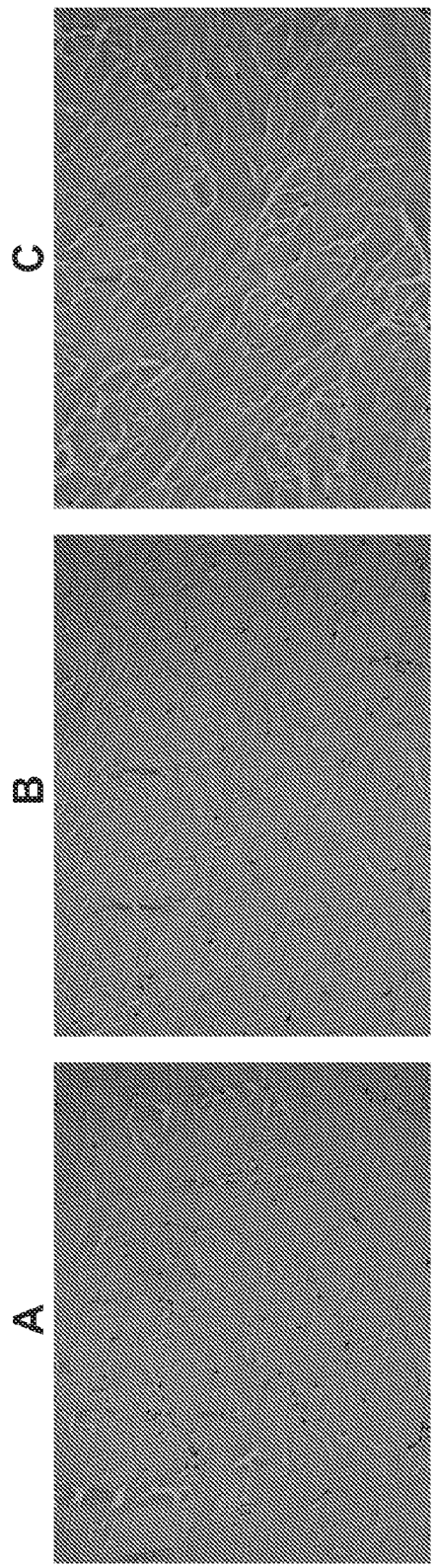

ELECTROPORATION OF TISSUE PRODUCTS

This application is a 35 U.S.C. §371 national stage filing of International Application No. PCT/US2014/010586, filed on Jan. 8, 2014, which claims priority under 35 U.S.C. §119 to U.S. Provisional Application No. 61/755,598, which was filed on Jan. 23, 2013, the content of each are herein incorporated in its entirety.

The present disclosure relates to methods for reducing bioburden on tissue products, and more particularly, to methods of reducing bioburden using electroporation, as well as tissue products produced according to the disclosed methods.

Human and animal tissues can be used to produce a variety of tissue products for patient use. When the tissues used in tissue products are procured from tissue banks or animal sources, they may contain undesirable levels of bacterial bioburden that must be reduced using various procedures. One option for reducing bioburden involves exposure to bactericides such as peracetic acid (PAA). High concentration and long duration exposure to bactericide, however, may be required to sufficiently reduce bioburden, which could lead, in some instances, to undesirable consequences such as damage to collagen networks or other tissue components. The bactericides may also suffer from an inability to adequately penetrate the bacterial cells or to reach bacteria growing throughout the full thickness of the tissue, leading to potential pockets of elevated bioburden in the final tissue product.

Accordingly, there is a need for improved methods of sterilizing and/or reducing the bioburden on a tissue product. Disclosed herein are methods comprising the use of electroporation to reduce bioburden and to enhance the effectiveness of one or more bactericides in reducing bioburden. In some instances, electroporation allows for an effective method of reducing bioburden and permits use of a lower concentration, duration, and/or total volume of bactericide. Further, the use of electroporation can allow for a more even administration of bactericide across the full thickness of the tissue product. Moreover, electroporation can also be used as part of a method of decellularizing a tissue product while simultaneously reducing bioburden.

In various embodiments, a method of reducing bioburden in a tissue product is provided, comprising providing a human or animal tissue, contacting the tissue with one or more bactericides, and exposing the tissue to one or more electrical pulses. The method can produce a substantial reduction in bioburden (e.g., a reduction of at least about 50%). In some embodiments, the duration of the electrical pulses, voltage of the electrical pulses, and number of electrical pulses can be controlled such that the extracellular matrix of the tissue product is not damaged during exposure to the electrical pulses. In some embodiments the duration of exposure to and concentration of the one or more bactericides are controlled such that the extracellular matrix of the tissue product is not damaged during exposure to the one or more bactericides. In certain embodiments, the method further comprises allowing the tissue to cool and then exposing the tissue to one or more additional electrical pulses.

In various embodiments, the bactericide comprises one or more microbial growth inhibitors, cytotoxic agents, oxidants, and/or antibiotics. In some embodiments, the bactericide comprises one or more of a peroxide, oxidizer, antimicrobial metal, quaternary ammonium compound, or charged bactericidal compound. In some embodiments, the bactericide comprises one or more of peracetic acid (PAA), ozone, hypochlorite, silver, zinc, copper, benzalkonium chloride, cetylpyridinium chloride, benzethonium chloride, cetyltrimethyl ammonium bromide, or chitosan. For example, the bactericide can comprise PAA, e.g., at a concentration of about 0.01%-2% weight/volume.

In various embodiments, the bactericide is applied to the tissue at a concentration sufficient to substantially reduce bioburden on the tissue. In some embodiments, the method of reducing bioburden further comprises irradiating the tissue using e-beam radiation. In some embodiments, the method further comprises decellularizing the tissue, for example by contacting the tissue with one or more detergents and/or by exposure to one or more electrical pulses.

In various embodiments, a tissue product is provided, comprising a human or animal tissue that has been contacted with one or more bactericides and exposed to one or more electrical pulses. In some embodiments, the bioburden on the tissue has been reduced by at least about 50%. In some embodiments, the tissue product comprises an intact extracellular matrix. In some embodiments, the tissue product has been irradiated using e-beam radiation. In some embodiments, the tissue product comprises decellularized tissue.

DESCRIPTION OF THE DRAWINGS

FIG. 1A-C show hematoxylin and eosin (H&E) staining of 1 cm by 1 cm samples of porcine dermis after exposure for 15 milliseconds to one electrical pulse of 0V (FIG. 1A), 40V (FIG. 1B), or 80V (FIG. 1C), according to certain embodiments of the present disclosure.

DESCRIPTION OF CERTAIN EXEMPLARY EMBODIMENTS

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included," is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Various human and animal tissues can be used to produce tissue products. For example, various tissue products have been produced for regeneration, repair, reinforcement, and/or treatment of human tissues that have been damaged or lost due to various diseases and/or structural damage (e.g., from trauma, surgery, atrophy, and/or long-term wear and degeneration). Likewise, such products have been used to augment or enhance various tissues. These products can include, for example, acellular tissue matrices, tissue allografts or xenografts, and/or reconstituted tissues (e.g., at least partially decellularized tissues that have been seeded with cells to produce viable materials). For example, ALLODERM® and STRATTICE™ (LifeCell Corp., Branchburg, N.J.) are two dermal acellular tissue matrices made from human and porcine dermis, respectively. In preparing these tissue products, there can be a need to reduce bioburden.

Disclosed herein are methods for reducing bioburden in a tissue product using electroporation, as well as the tissue products produced according to the disclosed methods. The method can involve providing a tissue from an animal (including a human tissue). The tissue can be processed to prepare a desired tissue product (e.g., by manually cutting, shaping, or molding the tissue product to a desired shape, by decellularizing the tissue, and/or by any other desired processing procedure). The tissue is treated to reduce bioburden before, at the same time, or after the processing step(s).

Treating a tissue to reduce bioburden can comprise administering one or more electrical pulses to the tissue. In some embodiments, the exposure to electrical pulses alone is sufficient to reduce, and/or substantially reduce, bioburden. Electroporation can be administered to a tissue that has been contacted with one or more chemical or biological bactericide agents. For example, a tissue product can be immersed in a solution containing PAA, and then one or more electrical pulses can be administered to the tissue product. In some embodiments, pulses of long duration, high voltage, and/or multiple pulses in rapid succession can create temporary or permanent pores in the lipid membranes of bacterial cell walls, resulting in cell death directly or through the subsequent penetrance of one or more bactericides into the microbial cell. A minimum voltage can be required to establish pores in bacterial cell walls. In addition, the pulse voltage, pulse duration, and/or number of pulses administered can regulate the size of pores and the amount of time that pores in bacterial cell walls remain open, with higher voltage, duration, and/or pulse number resulting in larger and more long-lasting pores.

In some embodiments, the use of electroporation allows for an efficient reduction in bioburden while using a lower concentration, volume, and/or exposure time of the one or more bactericide. For instance, the use of electrical pulses can destroy microbes on the tissue surface by degrading the microbial cell membranes. Likewise, the electrical pulses can open pores in the bacterial cell membranes through which one or more bactericide (e.g., PAA) can enter and destroy the microbes, allowing for a reduction in bioburden while using a reduced concentration of bactericide and/or shorter duration exposure to bactericide. In addition, electroporation may drive bactericide into the tissue, allowing for a reduction in bioburden more consistently along the full thickness of the tissue.

In some embodiments, the electroporation methods described above can be used in conjunction with a decellularization procedure. For instance, a tissue can be decellularized by exposure to one or more detergents and by exposure to electrical pulses, either simultaneously or sequentially. Both the electrical pulses and the detergent can be used to destroy and remove cellular material from the tissue, while at the same time the exposure to electrical pulses and bactericide can also reduce bioburden in the tissue undergoing processing.

In various embodiments, electroporation can include the administration of one or more high voltage pulses. The high voltage pulses can have a duration of about 1 millisecond (ms) to 1 second. For example, pulses of about 1-50 ms can be used (e.g., about 1, 2, 3, 4, 5, 10, 15, 20, 25, 30, 35, 40, 45, or 50 ms, or any time period in between). In certain embodiments, pulses of about 5 ms, 10 ms, or 15 ms in duration are used. In some embodiments, longer pulses are used in order to increase the percentage reduction in bioburden. The one or more pulses can be delivered at a voltage of about 1V-10 kV. For example, pulses of about 10V-100V can be used (e.g., about 10, 20, 30, 40, 50, 60, 70, 80, 90, or 100 V, or any voltage in between). In certain embodiments, pulses of about 40V or 80V are used. In some embodiments, higher voltage pulses are used to increase the percentage reduction in bioburden. Both direct current and alternating current can be used with the electroporation methods disclosed herein. In some embodiments where alternating current pulses are administered, frequencies of about 1-10 KHz can be used. In some embodiments, about 1-100,000 pulses are delivered. For example, about 1-500 pulses can be delivered (e.g., about 1, 2, 3, 4, 5, 10, 15, 20, 25, 30, 40, 50, 100, 200, 300, 400, or 500 pulses, or any value in between). In some embodiments, a higher number of pulses are used in order to increase the percentage reduction in bioburden.

In various embodiments, the upper limit on the voltage, duration, and/or number of electrical pulses applied to a tissue will depend on the sensitivity of the chosen tissue to the electric field (e.g., the amount of electrical energy that the tissue can absorb without damage). In various embodiments, the lower limit on the voltage, duration, and/or number of pulses is based upon the sensitivity of the targeted bacterial organism to the electric field (e.g., the amount of energy required to kill or otherwise inactivate the targeted bacteria). In some embodiments, the pulse duration, pulse voltage, and/or number of pulses are controlled to avoid damage to the collagen and other extracellular networks in the tissue, to prevent an excessive elevation in temperature or pH, and/or to prevent any other damage to the tissue. In some embodiments, an excessive elevation in temperature is an increase above about 42 degrees Celsius (e.g., above about 35, 36, 37, 38, 39, 40, 41, 42, 43, 44, 45, or 50 degrees Celsius). In some embodiments, an excessive increase in pH is an increase above about 7.5 (e.g., above about 7.4, 7.5, 7.6, 7.7, 7.8, 7.9, or 8.0). In certain embodiments, the voltage, duration, and/or number of pulses required to reduce bioburden will depend on the thickness of the tissue, with thicker and/or larger tissues requiring more joules of energy in order to reduce bioburden by a desired percentage.

In some embodiments, multiple rounds of electroporation are delivered to the tissue to reduce bioburden. In some embodiments, the tissue is allowed to cool to room temperature between rounds of electroporation.

In various embodiments, the electroporation methods disclosed herein comprise applying one or more bactericides (e.g., 1, 2, 3, 4, 5, or more) to a tissue and administering one or more high voltage pulses to the tissue. The bactericide can comprise any chemical or biological agent suitable for reducing bioburden (including microbial growth inhibitors, cytotoxic agents, oxidants, and/or antibiotics). In some embodiments, the bactericide is peracetic acid (PAA). In some embodiments the bactericide is any chemical or biological agent that functions through bacterial membrane perturbation or acts intracellularly on a microbe. Examples of suitable bactericides include peroxides (e.g., PAA), oxidizers (e.g., ozone, hypochlorite), antimicrobial metals (e.g., silver, zinc, copper), quaternary ammonium compounds (e.g., benzalkonium chloride, cetylpyridinium chloride, benzethonium chloride, cetyltrimethyl ammonium bromide), and/or other charged bactericidal compounds such as chitosan that can be driven by electroporation through the pores formed in bacterial cell membranes.

In some embodiments, the bactericide is applied to the tissue at a concentration sufficient to reduce bioburden, and/or to substantially reduce bioburden. In some embodiments, PAA is applied to the tissue at a concentration sufficient to reduce bioburden, and/or to substantially reduce bioburden. In certain embodiments, PAA is applied to the tissue at a concentration of about 0.01%-2% weight/volume to reduce bioburden on the tissue (e.g., about 0.01, 0.02, 0.03, 0.04, 0.05, 0.1, 0.15, 0.2, 0.25, 0.3, 0.35, 0.4, 0.45, 0.5, 0.55, 0.6, 0.7, 0.8, 0.9, 1.0, 1.5, or 2.0%, or any percentage in between). In certain embodiments, PAA is applied to the tissue at a concentration of about 0.2% (w/v).

In various embodiments, any device known in the art for the delivery of electrical energy can be used to electroporate a tissue. For example, conductive electroporation plates can be placed in parallel on either side of a tissue and one or more electrical pulses can be passed between the plates. In some embodiments, the electroporation plates comprise a conductive metal and are positioned in parallel around a tissue, with each plate about 1 mm from the edge of the tissue. In certain embodiments, the electroporation plates comprise a conductive metal having dimensions of about 1 cm×2 cm and each plate is positioned about 1 mm from the edge of a 1 mm thick sample of tissue.

In various embodiments, the administration of electrical pulses in combination with one or more bactericide can allow for a method of reducing bioburden while also reducing the concentration of bactericide and the voltage/duration of electricity. For instance, a high concentration or long duration exposure to PAA or other bactericides can be associated with undesirable damage to the collagen networks in a tissue product. Likewise, exposure to high voltage or prolonged exposure to an electrical field can damage a tissue product. In certain embodiments, these negative effects on the quality of a tissue can be avoided by using a bactericide in combination with electroporation. Accordingly, in some embodiments, electroporation can be used in combination with a bactericide to enable a reduction in bioburden while using a lower concentration or shorter duration exposure to bactericide. Likewise, in certain embodiments, electroporation can be used in combination with a bactericide to enable a reduction in bioburden while using shorter duration or lower energy pulses, or fewer total pulses. For example, a substantial reduction in bioburden can be achieved by contacting a tissue with at least about 0.1% PAA and then administering one or more electrical pulses of at least about 40V and at least about 5 ms in duration.

In various embodiments, the electroporation methods discussed above can be used to reduce bioburden on a tissue (i.e., to reduce the number of microorganisms growing on the tissue). In some embodiments, the methods substantially reduce bioburden. As used herein, a tissue that has "substantially reduced bioburden" means a tissue on which the concentration of growing microorganisms is less than 70%, 60%, 50%, 40%, 30%, 20%, 15%, 10%, 5%, 1%, 0.1%, 0.01%, 0.001%, or 0.0001% of that growing on untreated tissue.

The electroporation methods discussed above can, optionally, be used in combination with one or more additional methods for reducing bioburden, such as exposure to radiation ("irradiation"). Irradiation can be used to further reduce bioburden. In some embodiments, an absorbed dose of about 14-18 kGy of e-beam radiation or 25-30 kGy of gamma irradiation is delivered. In various embodiments, a tissue product is exposed to between about 5 Gy and 50 kGy of radiation (e.g., about 5, 10, 15, 20, 25, 30, 35, 40, 45, or 50 kGy, or any value in between). Suitable forms of radiation can include gamma radiation, E-beam radiation, and X-ray radiation. In some embodiments, E-beam irradiation is used. Other irradiation methods are described in U.S. Application 2010/0272782, the disclosure of which is hereby incorporated by reference in its entirety. Irradiation can be applied before, simultaneously, or after electroporation.

Various tissues can be used with the methods disclosed herein. For example, human tissue can be obtained from one or more cadavers, e.g., from dermal or subdermal sources. Suitable human tissue can also be obtained from live donors (e.g., with an autologous tissue). Other species that can serve as donors of acellular tissue include, without limitation, nonhuman primates (e.g., monkeys, baboons, or chimpanzees), pigs, cows, horses, goats, sheep, dogs, cats, rabbits, guinea pigs, gerbils, hamsters, rats, or mice. In some embodiments, tissue from more than one donor animal can be used. Tissue from animals genetically modified to lack one or more antigens, such as the immunogenic antigen alpha galactose, can also be used.

In various embodiments, the tissue can come from one or more of fascia, pericardial tissue, dura, umbilical cord tissue, placental tissue, cardiac valve tissue, ligament tissue, tendon tissue, arterial tissue, venous tissue, neural connective tissue, urinary bladder tissue, ureter tissue, skin, dermal tissue, muscle tissue, heart tissue, lung tissue, liver tissue, or intestinal tissue. In some embodiments, the tissue is dermis. In certain embodiments, the tissue is human or porcine dermis. In certain embodiments, the tissue is ALLODERM® or STRATTICE™ (LifeCell Corp., Branchburg, N.J.).

The electroporation methods described above can be used in conjunction with additional tissue processing procedures, such as a decellularization procedure. In some embodiments, the electroporation procedure is conducted before the decellularization procedure, while in other embodiments the electroporation procedure is conducted after the decellularization. In some embodiments, electroporation procedures are conducted both before and after decellularization. In some embodiments, the two procedures are conducted simultaneously. In some embodiments, the electroporation procedure can disintegrate the cellular material from a tissue product, and can therefore be used as part of a decellularization procedure, as well as a bioburden reduction procedure.

In various embodiments, the decellularization procedure that is used in combination with an electroporation procedure comprises placing the tissue in a decellularization solution to remove viable cells (e.g., epithelial cells, endothelial cells, smooth muscle cells, and fibroblasts, etc.) from the extracellular matrix in the tissue without damaging the biological and/or structural integrity of the extracellular matrix. The decellularization solution may contain an appropriate buffer, salt, an antibiotic, one or more detergents (e.g., TRITON X-100™, sodium dodecyl sulfate, sodium deoxycholate, polyoxyethylene (20) sorbitan mono-oleate, etc.), one or more agents to prevent cross-linking, one or more protease inhibitors, and/or one or more enzymes. In some embodiments, the decellularization solution comprises 0.1%, 0.2%, 0.3%, 0.4%, 0.5%, 1.0%, 1.5%, 2.0%, 2.5%, 3.0%, 3.5%, 4.0%, 4.5%, or 5.0% (or any percentage in between) of TRITON X-100® and, optionally, 10 mM, 15 mM, 20 mM, 25 mM, 30 mM, 35 mM, 40 mM, 45 mM, or 50 mM EDTA (ethylenediaminetetraacetic acid) (or any concentration in between). In some embodiments, the tissue is incubated in the decellularization solution at 25, 30, 31, 32, 33, 34, 35, 36, 37, 38, 39, 40, 41, or 42° C. (or any temperature in between), and optionally with gentle shaking at 10, 20, 30, 40, 50, 60, 70, 80, 90, 100, 110, 120, 130, 140, or 150 rpm (or any rpm in between). The incubation can be for 1, 2, 3, 4, 5, 6, 7, 8, 9, 10, 11, 12, 15, 20, 24, 36, or 48 hours (or any time in between). The length of time or concentration of detergent can be adjusted in order to partially or more fully decellularize the tissue.

Exemplary methods for decellularizing tissue are disclosed in U.S. Pat. No. 6,933,326 and U.S. Patent Application 2010/0272782, which are hereby incorporated by reference in their entirety.

After electroporation and optional tissue processing, the resulting tissue product can be further processed to provide a desired three dimensional shape (e.g., a sheet of tissue product). In some embodiments, a tissue product can be further processed to provide an anatomical shape useful for implanting into a targeted host tissue. For example, a spherical or cylindrical shape can be provided when the tissue product will be implanted following removal of a similarly shaped volume of native tissue.

EXAMPLES

The following examples serve to illustrate, and in no way limit, the present disclosure.

Example 1

Effect of Pulse Voltage on Electroporation

To determine the impact of pulse voltage on bacteria present on tissue samples, 1 cm by 1 cm pieces of porcine dermis (1 mm thickness) were electroporated in 2 ml of 0.2% peracetic acid (PAA) at three different pulse voltages: 0V, 40V and 80V. The 0V samples were used as a control condition. Electroporation plates (1 cm by 2 cm conducting metal plates) were set 2 mm apart and a 1 mm thick piece of tissue was placed between them. Electrical pulses were delivered for 10 ms. All conditions were tested in triplicates.

Following electroporation each piece of tissue was removed and rinsed in a PAA neutralizing wash for 5 minutes and then placed in 10 ml of phosphate buffered saline (PBS). The purpose of the neutralizing wash was to prevent further bacterial kill from residual PAA following electroporation that could confound the results.

Stomaching was used to extract the bacteria from each piece of tissue and bacteria counts were performed following incubation of culture plates for 2 days at 37° C. Stomaching is a mechanical extraction method used to remove microorganisms from samples of foods, fabrics, swabs, or other soft materials such as human or animal tissue. The sample and diluents (water/PBS or any other buffer that does not impact microorganism viability) are placed in a sterile bag which is vigorously agitated on its outer surfaces by paddles inside a stomaching machine. The resulting compression and shearing forces elute deep-seated bacteria. Once the agitation process is completed, samples of the eluent are taken for microbial enumeration and subsequent identification.

The tissue samples exposed to 40V and 80V pulse voltages had 0 bacteria. The bacterial colonies from the 0V condition were too numerous to count. Porcine dermis was also stained using hematoxylin and eosin (H&E). See FIG. 1. Histological examination of the stained samples demonstrated potential changes in the collagen structure following exposure to 80 volts, whereas there was no detectable change after exposure to 40 volts.

Example 2

Effect of Pulse Length on Electroporation

To determine the effect of pulse length on bioburden, 1 cm by 1 cm pieces of porcine dermis (1 mm thickness) were electroporated in 2 ml of 0.2% PAA at one of four pulse lengths: 0 ms, 5 ms, 10 ms, and 15 ms. 0 ms pulses were used as a control condition. All conditions were tested in triplicates.

Electroporation plates (1 cm by 2 cm conducting metal plates) were set 2 mm apart and a 1 mm thick piece of tissue was placed between them. Pulse voltage was set at 80V. Following electroporation each piece of tissue was removed and rinsed in a PAA neutralizing wash for 5 minutes and then placed in 10 ml of PBS.

Stomaching was used to extract the bacteria from each piece of tissue and bacteria counts were performed following incubation of culture plates for 2 days at 37° C. As shown in Table 1 below, increasing the pulse length resulted in a decrease of detectable bioburden, with reductions in observable bioburden ranging between 2 and 4 log. Minimal bacterial colony forming units (CFU) were detected on tissue samples following 15 ms pulse.

TABLE 1

| Pulse Length (ms) | # of Pulses | Viable Cell Count (CFU) |
| --- | --- | --- |
| 15 | 1 | <10 |
| 10 | 1 | 140 |
| 5 | 1 | 300 |
| 1 | 100 | 430 |
| 0 | — | 26000 |

The preceding examples are intended to illustrate and in no way limit the present disclosure. Other embodiments of the disclosed devices and methods will be apparent to those skilled in the art from consideration of the specification and practice of the devices and methods disclosed herein.

What is claimed is:

1. A method of reducing the bioburden in a tissue product, comprising
   providing a human or animal tissue;
   contacting the tissue with one or more bactericides; and
   exposing the tissue to one or more electrical pulses.

2. The method of claim 1, wherein the method produces a substantial reduction in bioburden on the tissue.

3. The method of claim 2, wherein the bioburden on the tissue is reduced by at least about 50%.

4. The method of claim 1, wherein the duration of the electrical pulses, voltage of the electrical pulses, and number of electrical pulses are controlled such that the extracellular matrix of the tissue product is not damaged during exposure to the electrical pulses.

5. The method of claim 1, wherein the duration of exposure to and concentration of the one or more bactericides are controlled such that the extracellular matrix of the tissue product is not damaged during exposure to the one or more bactericides.

6. The method of claim 1, wherein the duration of the electrical pulses, voltage of the electrical pulses, and number of electrical pulses are controlled such that the temperature of the tissue product does not rise above about 42 degrees Celsius.

7. The method of claim 1, wherein the duration of the electrical pulses, voltage of the electrical pulses, and number of electrical pulses are controlled such that the pH of the tissue product does not rise above about pH 8.

8. The method of claim 1, wherein the one or more electrical pulses have a voltage of about 1 volt (V) to about 10 kilovolts (kV).

9. The method of claim 1, wherein the one or more electrical pulses have a voltage of about 40V or 80V.

10. The method of claim 1, further comprising administering the one or more electrical pulses for about 1 millisecond (ms) to about 1 second.

11. The method of claim 1, wherein the one or more electrical pulses have a duration of about 5 ms, about 10 ms, or about 15 ms.

12. The method of claim 1, comprising administering about 1 to 100,000 electrical pulses.

13. The method of claim 1, comprising administering about 1 to 500 electrical pulses.

14. The method of claim 1, further comprising allowing the tissue to cool and then exposing the tissue to one or more additional electrical pulses.

15. The method of claim 14, further comprising repeating the exposure to one or more additional electrical pulses 2-5 times.

16. The method of claim 1, wherein the bactericide comprises one or more microbial growth inhibitors, cytotoxic agents, oxidants, and/or antibiotics.

17. The method of claim 1, wherein the bactericide comprises one or more of a peroxide, oxidizer, antimicrobial metal, quaternary ammonium compound, or charged bactericidal compound.

18. The method of claim 1, wherein the bactericide comprises one or more of peracetic acid (PAA), ozone, hypochlorite, silver, zinc, copper, benzalkonium chloride, cetylpyridinium chloride, benzethonium chloride, cetyltrimethyl ammonium bromide, or chitosan.

19. The method of claim 1, wherein the bactericide comprises PAA.

20. The method of claim 19, wherein the PAA is at a concentration of about 0.01%-2% weight/volume.

21. The method of claim 19, wherein the PAA is at a concentration of about 0.2% weight/volume.

22. The method of claim 1, wherein the bactericide is applied to the tissue at a concentration sufficient to substantially reduce bioburden on the tissue.

23. The method of claim 1, further comprising irradiating the tissue using e-beam radiation.

24. The method of claim 1, further comprising decellularizing the tissue.

25. The method of claim 24, wherein the tissue is decellularized by contact with one or more detergents and by exposure to the one or more electrical pulses.

* * * * *